US012788704B2

(12) United States Patent
Bae et al.

(10) Patent No.: US 12,788,704 B2
(45) Date of Patent: Nov. 10, 2026

(54) CERIUM OXIDE INORGANIC FILLER-REINFORCED POLYMER AND TWO-COMPONENT COSMETIC COMPOSITION USING SAME

(71) Applicant: LG HOUSEHOLD & HEALTH CARE LTD., Seoul (KR)

(72) Inventors: Su Whan Bae, Seoul (KR); Da Wa Jeong, Seoul (KR); Chang Woo Lee, Seoul (KR)

(73) Assignee: LG HOUSEHOLD & HEALTH CARE LTD., Seoul (KR)

(*) Notice: Subject to any disclaimer, the term of this patent is extended or adjusted under 35 U.S.C. 154(b) by 1202 days.

(21) Appl. No.: 17/763,028

(22) PCT Filed: Sep. 24, 2020

(86) PCT No.: PCT/KR2020/012949
§ 371 (c)(1),
(2) Date: Sep. 16, 2022

(87) PCT Pub. No.: WO2021/060868
PCT Pub. Date: Apr. 1, 2021

(65) Prior Publication Data

US 2023/0051053 A1 Feb. 16, 2023

(30) Foreign Application Priority Data

Sep. 24, 2019 (KR) ........................ 10-2019-0117269

(51) Int. Cl.
*A61K 8/89* (2006.01)
*A61K 8/06* (2006.01)
*A61K 8/19* (2006.01)
*A61K 8/25* (2006.01)
*A61K 8/36* (2006.01)
*A61Q 19/08* (2006.01)

(52) U.S. Cl.
CPC .................. *A61K 8/89* (2013.01); *A61K 8/06* (2013.01); *A61K 8/19* (2013.01); *A61K 8/25* (2013.01); *A61K 8/361* (2013.01); *A61Q 19/08* (2013.01); *A61K 2800/612* (2013.01); *A61K 2800/621* (2013.01)

(58) Field of Classification Search
None
See application file for complete search history.

(56) References Cited

U.S. PATENT DOCUMENTS

| | | | | |
|---|---|---|---|---|
| 10,835,464 | B2 * | 11/2020 | Lee | A61Q 17/04 |
| 11,291,287 | B2 * | 4/2022 | Samain | A45D 40/24 |
| 2007/0173595 | A1 | 7/2007 | Tsuji et al. | |
| 2008/0226572 | A1 * | 9/2008 | Cassin | A61K 8/8158 424/78.03 |
| 2012/0003287 | A1 | 1/2012 | Schlossman et al. | |
| 2012/0237461 | A1 | 9/2012 | Yu et al. | |
| 2012/0251600 | A1 * | 10/2012 | Yu | A61K 8/585 424/78.03 |
| 2018/0177712 | A1 * | 6/2018 | El-Khouri | A61K 8/895 |

FOREIGN PATENT DOCUMENTS

| | | | | | |
|---|---|---|---|---|---|
| JP | 2004-331962 | A | | 11/2004 | |
| KR | 10-2011-0133490 | A | | 12/2011 | |
| KR | 10-2019-0004813 | A | | 1/2019 | |
| KR | 10-2019-0048093 | A | | 5/2019 | |
| KR | 20190048093 | A | * | 5/2019 | A61K 8/27 |
| KR | 10-2019-0080413 | A | | 7/2019 | |
| WO | WO-2017207776 | A1 | * | 12/2017 | A45D 44/005 |

OTHER PUBLICATIONS

International Search Report, issued in PCT/KR2020/012949 dated Jan. 4, 2021.

* cited by examiner

*Primary Examiner* — Sahana S Kaup
*Assistant Examiner* — Ashlee E Wertz
(74) *Attorney, Agent, or Firm* — Birch, Stewart, Kolasch & Birch, LLP

(57) ABSTRACT

The present invention relates to a two-component cosmetic composition for wrinkle reduction. The two-component cosmetic composition for wrinkle reduction according to the present invention forms a coating having a sufficient strength to reduce a scrubbing phenomenon caused by external force and has a suitable viscosity as well as no cloudiness phenomena arising.

8 Claims, 3 Drawing Sheets

[Fig. 1]
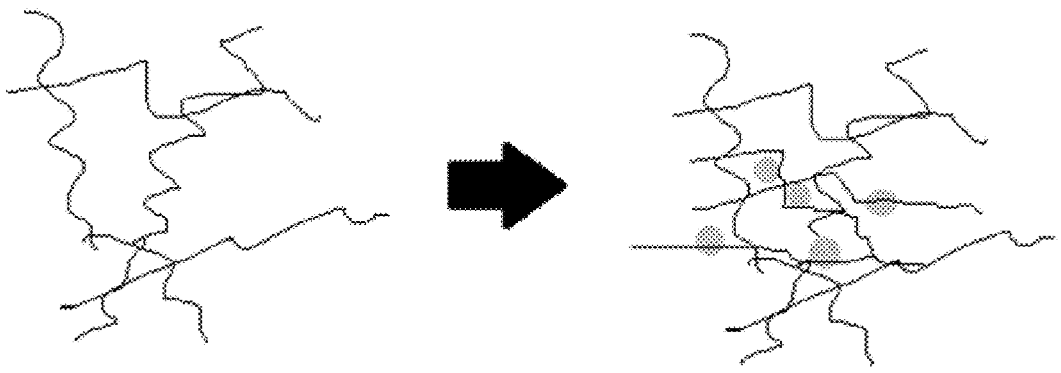
[Fig. 2]
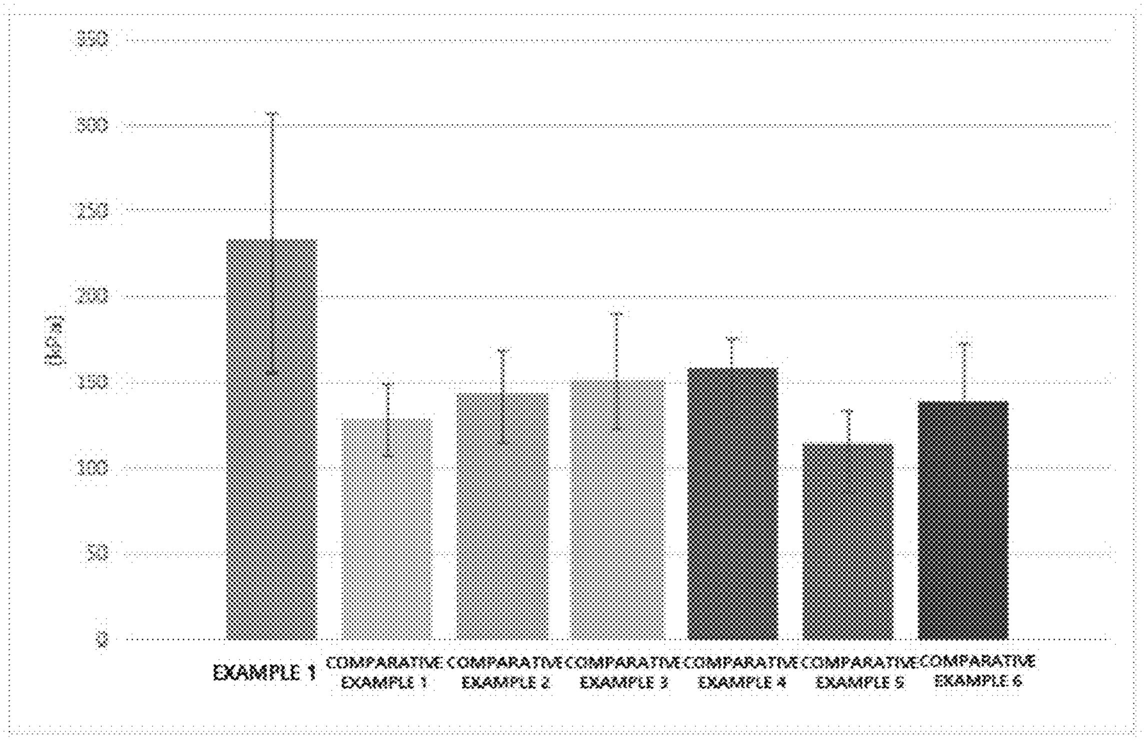

[Fig. 3]
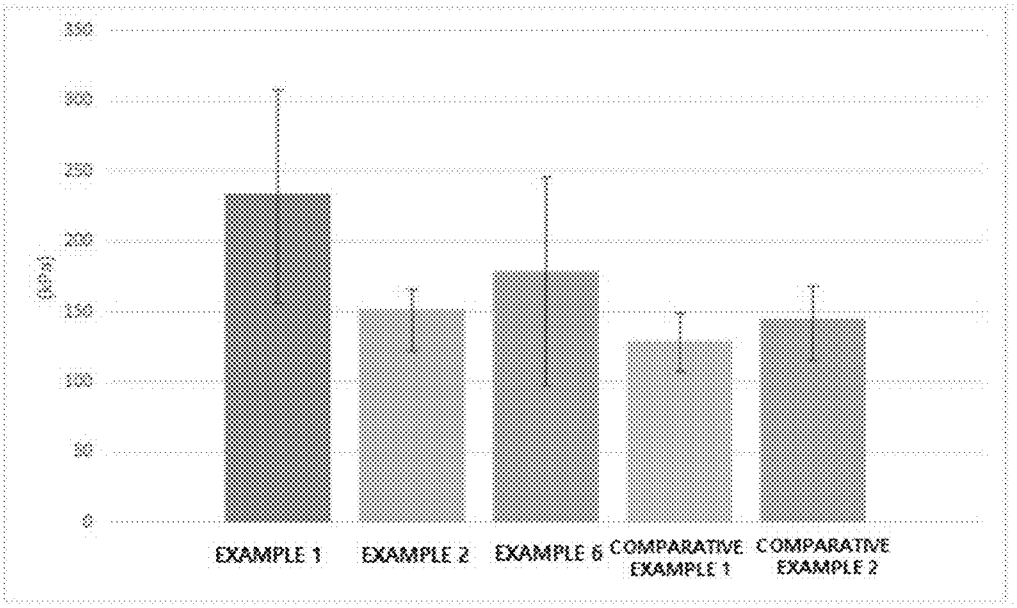
[Fig. 4]
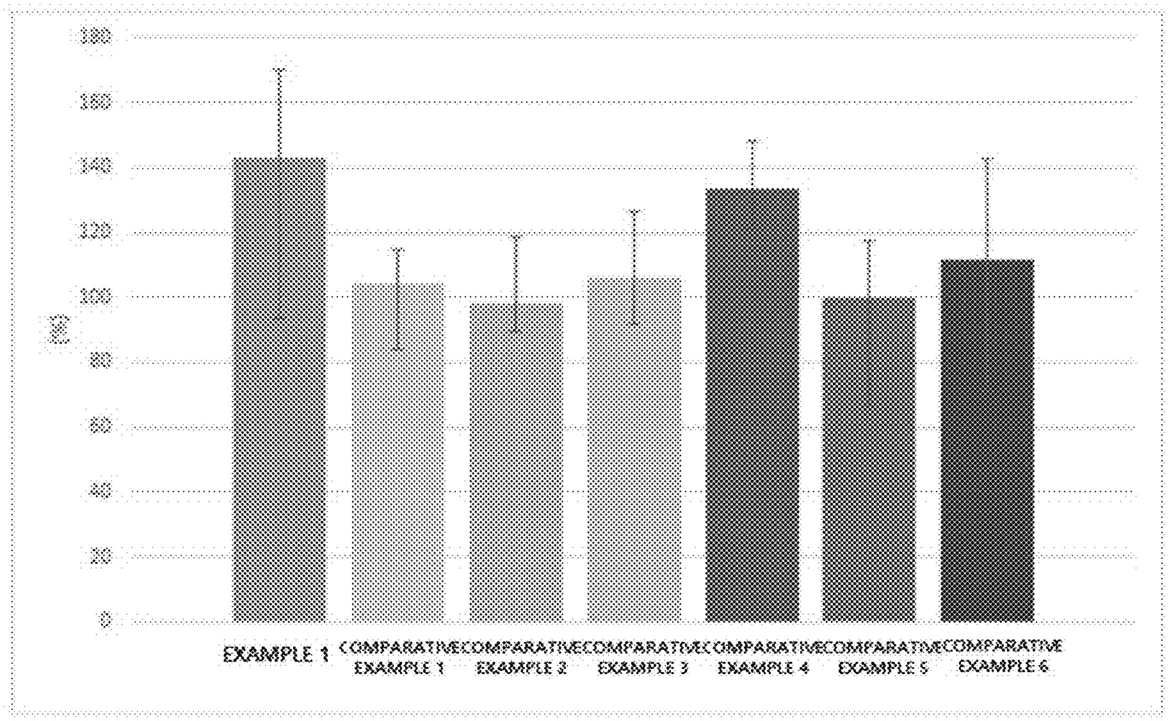

[Fig. 5]
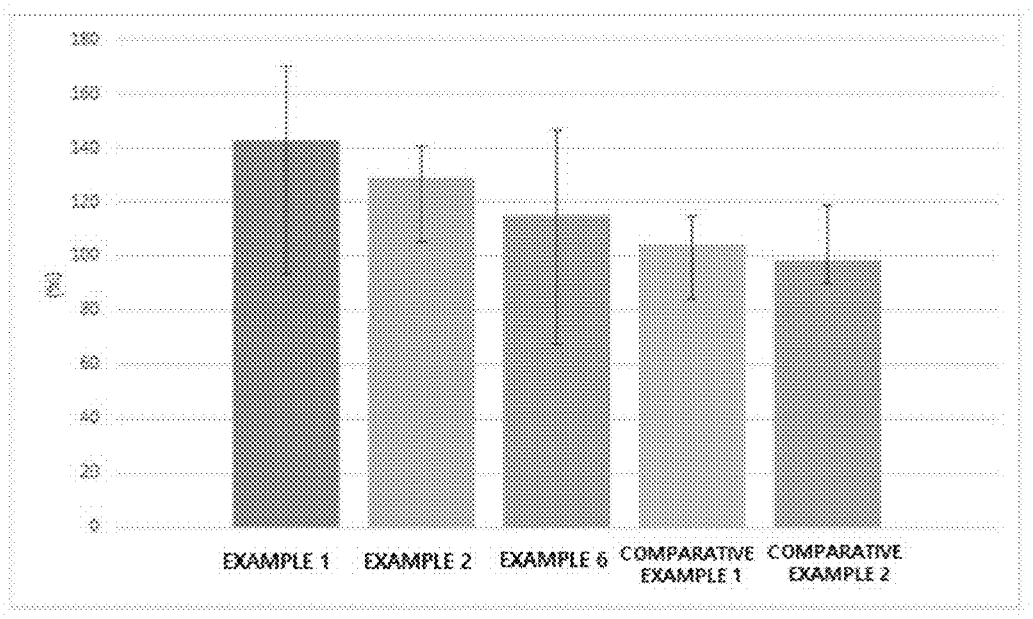
[Fig. 6]
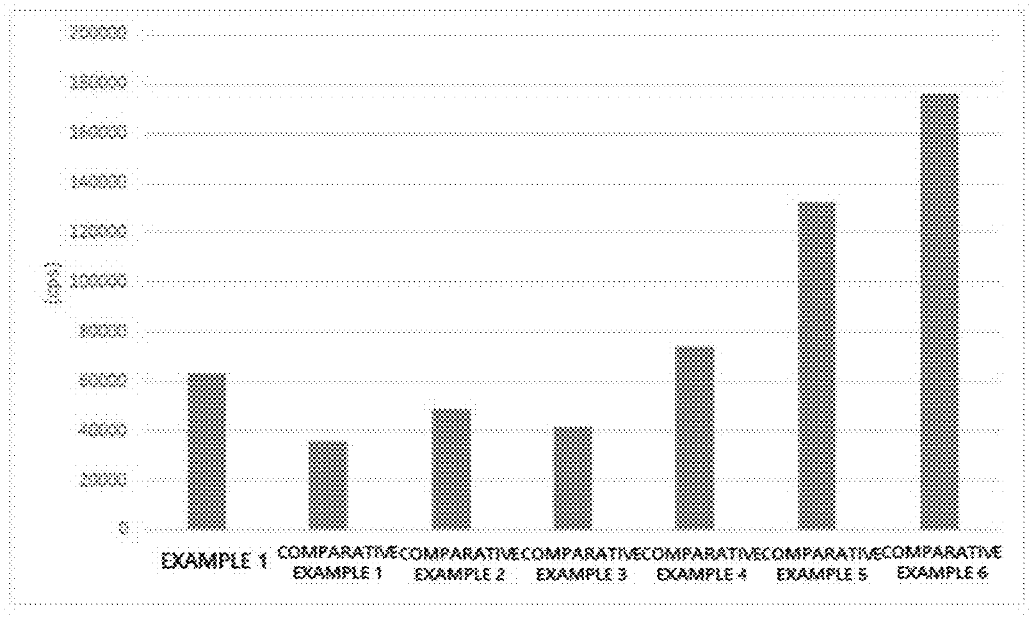

CERIUM OXIDE INORGANIC FILLER-REINFORCED POLYMER AND TWO-COMPONENT COSMETIC COMPOSITION USING SAME

TECHNICAL FIELD

The present invention relates to a cerium oxide inorganic filler-reinforced polymer and a two-component cosmetic composition for wrinkle improvement using the same.

BACKGROUND ART

A two-component addition polymerization-type room temperature vulcanizing silicone (hereinafter, referred to as RTV-2) is a kind of silicone polymer and is composed of a first agent including monomers for polymerization and a second agent including a metal catalyst, and it is possible to form a polymer through a polymerization reaction between monomers at room temperature or in a similar temperature range when the first agent and the second agent come into contact with each other. The RTV-2 has been used in various fields, such as the electric/electronics, construction, and molding fields, due to having excellent insulating and heat resistance properties.

(1) Patent Document 1 and Patent Document 2 enclose techniques for producing artificial skin or imparting smooth skin using RTV-2 in cosmetics as a result of forming a coating made of silicone rubber on the skin through in-situ room temperature polymerization. However, in the case of conventional techniques, the coating does not possess adequate mechanical properties, and thus the coating is damaged and detached by an external force. Therefore, the conventional techniques cannot solve the problem of the coating being recognized as dead skin when being scrubbed.

(2) In order to improve the mechanical properties of a polymer, fumed silica, carbon black, or metal oxides such as $TiO_2$ and ZnO have been conventionally added as a filler. However, since carbon black has a black color, it is difficult to use carbon black for the purpose of application on the face or other body sites due to concerns related to aesthetics, and fumed silica may increase the viscosity of a formulation to be more than is necessary when added to an RTV-2 cosmetic composition. In addition, since $TiO_2$ and ZnO are mainly used for the purpose of improving electrical and magnetic properties, thermal stability, and the like, the effect of increasing the mechanical durability of a coating is poor, and $TiO_2$ and ZnO may cause an unnatural reflection phenomenon resulting from having a high refractive index, which is referred to as a clouding phenomenon.

(3) In the case of Patent Document 1, an attempt is made to increase the strength of a coating by adding nano-sized fibrous cellulose, carboxymethyl cellulose, hydroxypropyl cellulose, or the like. However, there are problems in that viscosity increases due to the addition of cellulose, which is a thickening agent, cellulose is not easily dispersed compared to fillers having little or no thickening effect, and the effect of the increase in strength of a coating is insufficient.

Therefore, in order to provide an effect of imparting smooth skin and concealing wrinkles with respect to a user, a cosmetic composition that a) forms a coating having strength sufficient to prevent a scrubbing phenomenon, b) does not show a noticeable clouding phenomenon, and c) provides ease of viscosity control is required.

RELATED-ART DOCUMENTS

Patent Documents

1. Korean Registered Patent No. 10-1840254
2. Korean Registered Patent No. 10-1935060

DISCLOSURE

Technical Problem

As a result of repeated experiments and research to solve the above-described problems, the inventors of the present invention have found that, when cerium oxide ($CeO_2$) inorganic particles are used, 1) the mechanical properties of a polymer, that is, an RTV-2 coating, can be significantly improved through the interaction between cerium oxide and a polymer and accompanying phenomena, 2) the clouding phenomenon is highly suppressed compared to $TiO_2$ (rutile), as the refractive index of cerium oxide is about 2.05 and the refractive index of $TiO_2$ (rutile) is about 2.72, and 3) it is easier to control an increase in the viscosity of the formulation, as the viscosity rise in the first or second agent is less when using cerium oxide compared to cases when fumed silica or cellulose is used.

Therefore, the inventors of the present invention have confirmed that, when cerium oxide is applied as an inorganic filler to a polymer, especially RTV-2, it is possible to prepare a formulation that solves the above technical problems, that is, a formulation (cosmetic composition) that forms a coating having strength sufficient to improve a scrubbing phenomenon caused by an external force, does not show a noticeable clouding phenomenon, and has appropriate viscosity, and thus the inventors have completed the present invention.

Technical Solution

One aspect of the present invention provides a two-component cosmetic composition for wrinkle improvement, which includes a first silicone compound represented by Chemical Formula 1, a second silicone compound represented by Chemical Formula 3, cerium oxide ($CeO_2$), and a catalyst and is composed of a first agent and a second agent, wherein the second agent includes the catalyst, and wherein the catalyst, the first silicone compound, and the second silicone compound are not included in the same agent at the same time.

[Chemical Formula 1]

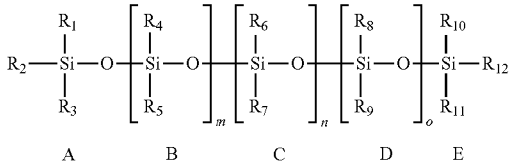

[Chemical Formula 3]

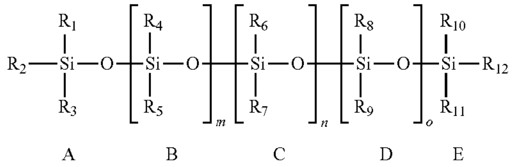

In Chemical Formula 1, $R_7$, $R_8$, and $R_9$ are vinyl groups, and $R_4$, $R_5$, and $R_6$ are each independently a hydrogen group, a methyl group, or a C2 to C20 linear or branched alkyl group, and when one or more of $R_1$, $R_2$, $R_3$, $R_{10}$, $R_{11}$, and $R_{12}$ are vinyl groups, m, n, and o are each independently an integer greater than or equal to 0, and when $R_1$, $R_2$, $R_3$, $R_{10}$, $R_{11}$, and $R_{12}$ are not vinyl groups, m is an integer greater than or equal to 0, and n+o is an integer greater than or equal to 1, and in Chemical Formula 3, $R_7$, $R_8$, and $R_9$ are hydrogen groups, and $R_4$, $R_5$, and $R_6$ are each independently a methyl group or a C2 to C20 linear or branched alkyl group, and when one or more of $R_1$, $R_2$, $R_3$, $R_{10}$, $R_{11}$, and $R_{12}$ are hydrogen groups, m, n, and o are each independently an integer greater than or equal to 0, and when $R_1$, $R_2$, $R_3$, $R_{10}$, $R_{11}$, and $R_{12}$ are not hydrogen groups, m is an integer greater than or equal to 0, and n+o is an integer greater than or equal to 1.

Another aspect of the present invention provides a method of improving wrinkles using the above-described two-component cosmetic composition for wrinkle improvement, which includes applying a first agent on the skin; and applying a second agent on the first agent.

Advantageous Effects

A two-component cosmetic composition for wrinkle improvement according to the present invention forms a coating having strength sufficient to improve a scrubbing phenomenon caused by an external force, does not show a noticeable clouding phenomenon, and has appropriate viscosity.

DESCRIPTION OF DRAWINGS

FIG. 1 is a conceptual diagram illustrating the change in polymer properties resulting from the addition of a filler.

FIGS. 2 and 3 show the results of measuring the breaking stress of coatings formed of compositions of the examples and comparative examples, and FIGS. 4 and 5 show results of measuring the breaking strain of coatings formed of compositions of the examples and comparative examples.

FIG. 6 shows the results of measuring the formulation viscosity of the first agents of the examples.

MODES OF THE INVENTION

The present invention relates to a two-component cosmetic composition for wrinkle improvement (hereinafter, referred to as cosmetic composition), which includes a first silicone compound represented by Chemical Formula 1, a second silicone compound represented by Chemical Formula 3, cerium oxide ($CeO_2$), and a catalyst and is composed of a first agent and a second agent, wherein the second agent includes the catalyst, and wherein the catalyst, the first silicone compound, and the second silicone compound are not included in the same agent at the same time.

[Chemical Formula 1]

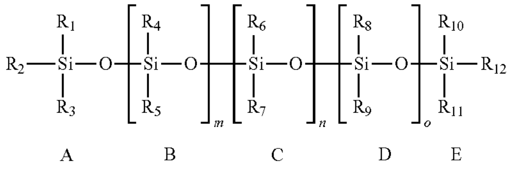

-continued

[Chemical Formula 3]

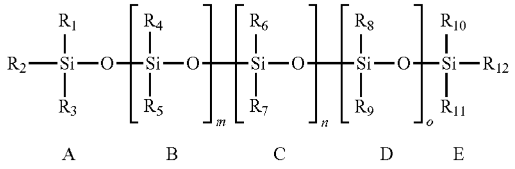

Hereinafter, the configuration of the present invention will be described in detail.

In the present invention, "wrinkle improvement" refers to providing an immediate wrinkle improvement effect by concealing wrinkles. The cosmetic composition of the present invention may have a wrinkle improvement effect because the composition penetrates into skin wrinkles in the treatment area to partially fill the wrinkles, is cured to form a coating, and thus provides an immediate wrinkle concealment effect. In addition, the composition of the present invention may have an effect of correcting problems related to skin shape by causing wrinkles, open pores, and roughness of the skin texture to become unseen, and can provide an effect of imparting smooth skin to a user.

The cosmetic composition of the present invention includes a first silicone compound represented by Chemical Formula 1, a second silicone compound represented by Chemical Formula 3, cerium oxide, and a catalyst, and these components will be described below.

Silicone Compound

In order to provide an effect of imparting smooth skin and immediately concealing wrinkles with respect to a user as a result of forming a coating through curing on a skin surface, factors such as affinity to the skin, adhesion, curing speed, temperature and humidity required for curing, and the physical and chemical strength of the coating needs to be considered. As a material that satisfies the said factors in the present invention, silicone, specifically, room temperature vulcanizing (RTV) silicone, may be used.

The RTV silicone may be roughly divided into (A) a one-component silicone composed only of a first agent and (B) a two-component silicone composed of a first agent and a second agent and used by mixing the two agents. In addition, the RTV silicone may be divided into two types, (a) a condensation polymerization type and (b) an addition polymerization type based on the type of reaction that occurs during the curing process. Among them, a one-component condensation polymerization-type RTV silicone (A-a) and a two-component condensation polymerization-type RTV silicone (B-a) require moisture during curing and thus have a problem in that the curing speed changes based on humidity and in that gas odor is generated during the curing process due to gaseous by-products such as alcohol or the like. Therefore, they are not suitable for application in the formulation of the present invention, which is applied to the skin. In addition, the one-component addition polymerization-type RTV silicone (A-b) has a limitation related to storage temperature and requires a heating process for fast curing for the sake of user convenience and immediate exhibition of effects, and therefore, it is not suitable for application in the formulation of the present invention, which is used on the skin surface.

The two-component addition polymerization-type RTV silicone (B-b), that is, RTV-2, is preferable for application in the formulation of the present invention because a first agent and a second agent are separately stored, and curing is initiated by mixing the first agent and the second agent and proceeds at room temperature without comprising a heating process due to the presence of a catalyst. In addition, it is easy to control the curing speed as a result of controlling the concentration of the catalyst in the second agent. Therefore, in the present invention, RTV-2 among the above-described RTV silicones can be easily applied to the skin.

In order to use RTV-2, the cosmetic composition of the present invention may include a first silicone compound and a second silicone compound.

The first silicone compound refers to a compound including one or more unsaturated bonds, specifically, vinyl groups, in the structure thereof, and the second silicone compound refers to a compound including one or more hydrogen groups in the structure thereof. The first silicone compound and the second silicone compound may be cured through the use of addition polymerization, specifically, hydrosilylation, in order to form RTV-2.

In an embodiment of the present invention, the first silicone compound may be represented by the following Chemical Formula 1. Chemical Formula 1 shows the general structure of a silicone compound including unsaturated bonds used for hydrosilylation in RTV-2.

[Chemical Formula 1]

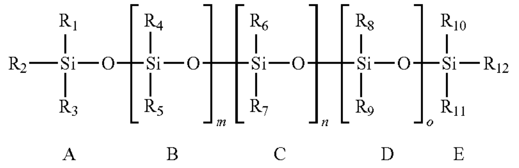

In Chemical Formula 1, at least one of $R_1$, $R_2$, $R_3$, $R_4$, $R_5$, $R_6$, $R_7$, $R_8$, $R_9$, $R_{10}$, $R_{11}$, and $R_{12}$ may be an unsaturated carbon double bond, specifically, a vinyl group. In Chemical Formula 1, $R_7$, $R_8$, and $R_9$ may be vinyl groups, $R_4$, $R_5$, and $R_6$ may each independently be a hydrogen group, a methyl group, a C2 to C20 linear or branched alkyl group, or other functional groups excluding a vinyl group. In Chemical Formula 1, when one or more of $R_1$, $R_2$, $R_3$, $R_{10}$, $R_{11}$, and $R_{12}$ are vinyl groups, the remainder of $R_1$, $R_2$, $R_3$, $R_{10}$, $R_{11}$, and $R_{12}$, which are not vinyl groups, may each independently be a hydrogen group, a methyl group, a C2 to C20 linear or branched alkyl group, or other functional groups excluding a vinyl group. In Chemical Formula 1, m, n, and o represent the number of monomers B, C, and D constituting the silicone compound having unsaturated bonds, respectively. m, n, and o may each be an integer greater than 0. In Chemical Formula 1, when one or more of $R_1$, $R_2$, $R_3$, $R_{10}$, $R_{11}$, and $R_{12}$ are vinyl groups, m+n+o may be an integer greater than or equal to 0, that is, m, n, and o may each independently be an integer greater than or equal to 0. In addition, in Chemical Formula 1, when none of $R_1$, $R_2$, $R_3$, $R_{10}$, $R_{11}$, and $R_{12}$ is a vinyl group, m may be an integer greater than or equal to 0, and n+o may be an integer greater than or equal to 1 (that is, one or more of the monomer C and the monomer D may be included). The distribution and order of monomers B, C, and D constituting the chain may be continuous, discontinuous, repetitive, or random depending on the characteristics of the polymerization reaction used to prepare the polymer.

In an embodiment of the present invention, the first silicone compound may be represented by the following Chemical Formula 2. Chemical Formula 2 represents a compound having one or more vinyl groups in parts A and E, that is, a vinyl-terminated compound.

[Chemical Formula 2]

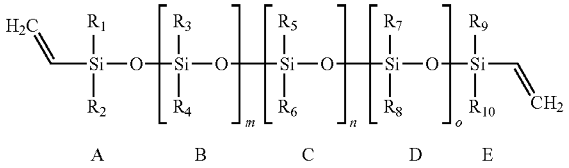

In Chemical Formula 2, $R_1$ to $R_{10}$ may each independently be a vinyl group, a hydrogen group, a methyl group, a C2 to C20 linear or branched alkyl group, or other functional groups excluding a vinyl group. Specifically, $R_6$, $R_7$, and $R_8$ may be vinyl groups, and $R_3$, $R_4$, and $R_5$ may each independently be a hydrogen group, a methyl group, a C2 to C20 linear or branched alkyl group, or other functional groups excluding a vinyl group. In Chemical Formula 2, $R_1$, $R_2$, $R_9$, and $R_{10}$ may each independently be a vinyl group, a hydrogen group, a methyl group, a C2 to C20 linear or branched alkyl group, or other functional groups excluding a vinyl group. m, n, and o may each be an integer greater than 0, and m+n+o may be an integer greater than or equal to 0. The distribution and order of monomers B, C, and D constituting the polymer chain may be continuous, discontinuous, repetitive, or random depending on the characteristics of a polymerization reaction used to prepare the polymer.

In an embodiment, the first silicone compound may have a viscosity or kinematic viscosity of 5 to 165,000 cps or cSt, specifically, 20 to 100,000 cps or cSt. In addition, a silicone compound having a viscosity or kinematic viscosity of 100 to 500 cps or cSt and a silicone compound having a viscosity or kinematic viscosity of 50,000 to 100,000 cps or cSt may be used alone or in combination. Moreover, a vinyl equivalent in the first silicone compound may be 0.01 to 5 mmol/g, specifically, 0.015 to 1.5 mmol/g or 0.02 to 0.5 mmol/g.

As the first silicone compound, vinyl dimethicone may be used, and commercially available examples of the first silicone compound include the Andisil® VS series from AB Specialty Silicones, but is not limited thereto.

In an embodiment of the present invention, the second silicone compound may be represented by the following Chemical Formula 3. Chemical Formula 3 shows the general structure of a silicone compound having hydrogen groups used for hydrosilylation in RTV-2.

[Chemical Formula 3]

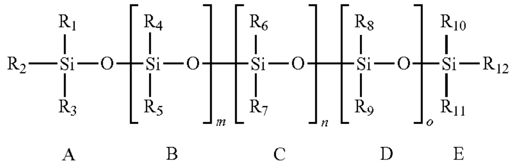

In Chemical Formula 3, at least one of $R_1$, $R_2$, $R_3$, $R_4$, $R_5$, $R_6$, $R_7$, $R_8$, $R_9$, $R_{10}$, $R_{11}$, and $R_{12}$ may be hydrogen. In Chemical Formula 3, $R_7$, $R_8$, and $R_9$ may be hydrogen groups, and $R_4$, $R_5$, and $R_6$ may each independently be a methyl group, a C2 to C20 linear or branched alkyl group, or other functional groups. In Chemical Formula 3, when one or more of $R_1$, $R_2$, $R_3$, $R_{10}$, $R_{11}$, and $R_{12}$ are hydrogen groups, the remainder of $R_1$, $R_2$, $R_3$, $R_{10}$, $R_{11}$, and $R_{12}$, which are not hydrogen groups, may each independently be a methyl group, a C2 to C20 linear or branched alkyl group, or other functional groups. m, n, and o represent the number of monomers B, C, and D constituting the silicone compound having hydrogen groups, respectively. In Chemical Formula 3, when one or more of $R_1$, $R_2$, $R_3$, $R_{10}$, $R_{11}$, and $R_{12}$ are hydrogen, m, n, and o may be integers greater than 0, that is, m+n+o may be an integer greater than or equal to 0. In addition, in Chemical Formula 3, when $R_1$, $R_2$, $R_3$, $R_{10}$, $R_{11}$, and $R_{12}$ are not hydrogen groups, m may be an integer greater than or equal to 0, and n+o may be an integer greater than or equal to 1. The distribution and order of monomers B, C, and D constituting the chain may be continuous, discontinuous, repetitive, or random depending on the characteristics of a polymerization reaction used to prepare the polymer.

In an embodiment of the present invention, the second silicone compound may be represented by the following Chemical Formula 4. Chemical Formula 4 may have random pendant silicon-hydride functional groups having three methyl groups (end-capped with trimethylsiloxy groups) in parts A and E.

[Chemical Formula 4]

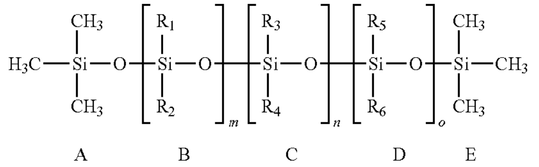

In Chemical Formula 4, $R_4$, $R_5$, and $R_6$ may be hydrogen groups, $R_1$, $R_2$ and $R_3$ may each independently be a methyl group, a C2 to C20 linear or branched alkyl group, or other functional groups. m may be an integer greater than or equal to 0, and n+o may be an integer greater than or equal to 1. The distribution and order of monomers B, C, and D constituting the chain may be continuous, discontinuous, repetitive, or random depending on the characteristics of a polymerization reaction used to prepare the polymer.

In an embodiment, the second silicone compound may have a viscosity or a kinematic viscosity of 5 to 5,000 cps or cSt, specifically, 10 to 2,500 cps or cSt or 25 to 1,000 cps or cSt. In addition, a hydrogen group equivalent, that is, Si—H, in the second silicone compound may be 0.1 to 20 mmol/g, specifically, 0.2 to 10 mmol/g or 0.5 to 8 mmol/g.

As the second silicone compound, hydrogen dimethicone may be used, and examples of the second silicone compound that are commercially available include the Andisil® XL series and Andisil® CE series from AB Specialty Silicones, but is not limited thereto.

In an embodiment, the first silicone compound and the second silicone compound may be cured through addition polymerization in the presence of a catalyst. The following Reaction Scheme 1 shows the curing principle of RTV-2.

[Reaction Scheme 1]

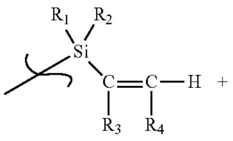

-continued

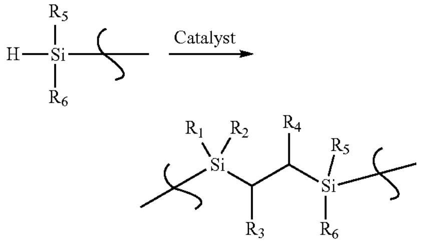

In Reaction Scheme 1, $R_1$, $R_2$, $R_3$, $R_4$, $R_5$, and $R_6$ may each be hydrogen, an alkyl group, or other functional groups.

As shown in Reaction Scheme 1, the curing of a compound having carbon double bonds (i.e., first silicone compound) in the chain and a compound having hydrogen groups (i.e., second silicone compound) in the chain may be performed through addition polymerization in the presence of a catalyst. Specifically, a silicone compound having unsaturated bonds, for instance, a vinyl group (e.g, vinyl dimethicone) and a silicone compound having hydrogen groups (e.g, hydrogen dimethicone) may be subjected to addition polymerization and cured. The reaction is, for example, curing through the addition of an Si—H bond to an unsaturated bond in the presence of a catalyst, that is, hydrosilylation.

Catalyst

In the present invention, the above-described addition polymerization of the first silicone compound and the second silicone compound may be performed using a catalyst. The catalyst may be a catalyst capable of promoting a hydrosilylation reaction in a formulation to provide an effect of immediately imparting smooth skin and concealing wrinkles with respect to a consumer through the formation of a coating at room temperature.

In an embodiment, the catalyst may be a metal catalyst including a metal ion or a metal atom in a molecular or crystalline structure thereof. In this case, the metal may be platinum (Pt). Specifically, the catalyst may be a platinum catalyst including platinum (Pt) in the molecular or crystalline structure. As the platinum catalyst that promotes a hydrosilylation reaction, for example, Karstedt's catalyst may be used. The structure of Karstedt's catalyst may be represented by Chemical Formula 5.

[Chemical Formula 5]

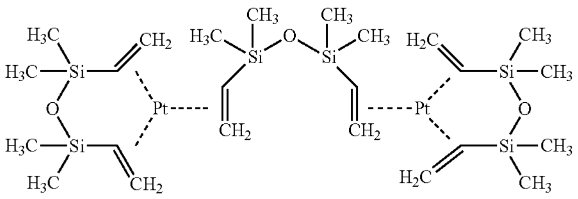

In the present invention, the metal catalyst that is used to promote a hydrosilylation reaction is not limited to Karstedt's catalyst.

In an embodiment, the catalyst may be used alone or as a catalyst composition containing the catalyst. For example, in an embodiment of the present invention, a platinum(tetramethyldivinyldisiloxane) solution in 200 cSt vinyl-terminated poly(dimethylsiloxane) (2% Pt) is used, which is a catalyst composition including 2% of the Pt catalyst.

In an embodiment, the catalyst may be included in an amount of 10 to 600 ppm, specifically, 20 to 400 ppm or 20 to 200 ppm, in the second agent to be described below.

Filler

The description related to a filler used in a polymer is the same as that described in Non-Patent Documents 1 to 3.

[Non-Patent Document 1] Non-Linear Viscoelasticity of Rubber Composites and Nanocomposites; Influence of Filler Geometry and Size in Different Length Scales (Deepalekshmi Ponnamma et al.).

[Non-Patent Document 2] The Reinforcement of Elastomeric Networks by Fillers (Liliane Bokobza, Macromolecular Materials and Engineering, 2004, 289, 607-621)

[Non-Patent Document 3] Cerium Oxide for Sunscreen Cosmetics (Shinryo Yabe et al., Journal of Solid Chemistry, 2003, 171, 7-11)

As described in Non-Patent Document 1, as a filler for improving the mechanical, optical, and electromagnetic properties of a polymer, inorganic fillers such as fumed silica, ZnO, and $TiO_2$, carbon black, carbon nanotubes, or the like may be used. In terms of the modification of the mechanical properties of a polymer, generally, the better the dispersion of the filler, the stronger the interaction between the surface of the filler particle and the polymer matrix, and the greater the surface area of the filler interacting with the polymer, a filler modification effect may increase. Although the principle or mechanism for the reinforcement of the properties, particularly, mechanical properties, of the filler for the polymer, is not completely configured, as shown in Non-Patent Document 2, it is known that the filler-polymer interaction, due to filler particles, may cause additional crosslinking of the polymer and limit movement of the chain in a high strain section to change the behavior pattern of the polymer. In the present invention, FIG. 1 is a conceptual diagram illustrating a change in polymer properties resulting from the addition of the filler.

In the present invention, as the filler, cerium oxide ($CeO_2$) is used. In the present invention, cerium oxide is an oxide of cerium, is a type of metal oxide, and is a solid at room temperature and atmospheric pressure. The oxidation number of cerium when represented by the chemical formula $CeO_2$ is IV, but the oxidation number of each cerium atom in the structure may be slightly increased or decreased depending on the presence or absence of oxygen vacancy inside based on production conditions of $CeO_2$.

Cerium oxide is generally used as a metal oxide additive in fields such as those related to electrodes of secondary batteries or fuel cells and catalysts for exhaust gas purification. Even when cerium oxide is used as a filler for a polymer, only the thermal and electrical/magnetic properties changed by the cerium oxide has been the focus of attention, and the use for modifying optical properties, particularly, physical properties, has not been known until now. Even when cerium oxide is used in cosmetics, the cerium oxide has been used as a white pigment or an inorganic pigment for UV protection in a cosmetic composition, and the use for improving the optical/physical properties of a polymer has not been known until now.

That is, the present invention is characterized by using cerium oxide to improve the properties of a polymer, that is, an RTV-2 coating, and applying the coating to a cosmetic formulation.

Therefore, the cerium oxide of the present invention is added as an additive for improving the properties of a cosmetic composition, particularly, for improving the mechanical properties (specifically, tensile strength and elongation rate) of an RTV-2 coating. Particularly, the cerium oxide may be used to prepare a formulation that is able to overcome the scrubbing phenomenon of a coating caused by an external force based on improving tensile strength. As described in an example below, an improvement in the properties of an RTV-2 coating through cerium oxide is very significant compared to that of a conventional filler. In addition, as shown in Non-Patent Document 3, cerium oxide, having a refractive index of about 2.05, causes less cloudiness compared to using the same amount of $TiO_2$, which has a refractive index of 2.72, exhibits less viscosity increase of the formulation relative to cases using fumed silica or cellulose, and improves the strength of a coating to a surprising level when added to the first agent or second agent of RTV-2.

In an embodiment, the cerium oxide may have an average particle diameter of 50 nm to 20 μm, specifically, 70 nm to 15 μm or 90 nm to 10 μm, when measured through dynamic light scattering (DLS) or scanning electron microscopy (SEM). In consideration of the maximization of the filler-polymer interaction and the dispersibility of the filler, the average particle diameter of cerium oxide should preferably be within the above range.

In an embodiment, the cerium oxide may be surface-modified.

The surface-modified cerium oxide may be treated by polyhydroxystearic acid, stearic acid, alkyl silane, fatty acid, or a silane coupling agent, or may be a silica-coated cerium oxide. Alternatively, cerium oxide that has been subjected to at least two types of surface treatments (modifications) may be used. In this case, polyhydroxystearic acid, stearic acid, an alkyl silane, a fatty acid, a silane coupling agent, or silica is used as a surface treatment agent, and a surface treatment (modification) method may be a general method in the art. Although the surface treatment that can be used in the present invention is not limited thereto, surface treatments typically used in the art may be used alone or in combination to maximize the filler-polymer interaction and the dispersibility of the filler, thereby increasing an improvement in mechanical properties, preventing the re-agglomeration of filler particles, or improving other properties and functional characteristics of a formulation.

In an embodiment, the total amount of the surface treatment agent may be 0.1 to 50% by mass with respect to the total mass of the surface-treated cerium oxide.

In an embodiment, although the form of cerium oxide is not particularly limited, cerium oxide may be in the form of solid powder or in a dispersed form in water, hydrocarbon-based oil, silicone-based oil, ester-based oil, or other solvents.

In an embodiment, when the cerium oxide is in a dispersed form in a solvent, that is, water, oil, or the like, a pH controller, a thickener, or other dispersion stabilizers may be further added, or the surface of cerium oxide may be further treated for the purpose of preventing aggregation and precipitation of cerium oxide and increasing the stability of the dispersion.

As described above, the cosmetic composition according to the present invention includes the first silicone compound, the second silicone compound, the catalyst, and the cerium oxide.

In addition, the cosmetic composition according to the present invention is a two-component type composition, that is, composed of a first agent and a second agent, to control curing.

In an embodiment, the second agent includes the catalyst. The first agent may include both or one of the two components for a hydrosilylation reaction, that is, the first silicone compound and the second silicone compound, and when the first agent includes only one of the two components, the other component may be included in the second agent. Since the silicone compounds according to the present invention may be cured at room temperature in the presence of a catalyst, when the catalyst and two silicone compounds are all included in the second agent, there is a concern that polymerization may be initiated before the second agent and the first agent are mixed, that is, even when a user does not desire it. Therefore, it is preferable to avoid the simultaneous inclusion of the catalyst, the first silicone compound, and the second silicone compound in a formulation prior to use. In addition, the cerium oxide may be included in the first agent or the second agent.

In an embodiment, when RTV-2 is formulated, particularly, when the resulting formulation is an emulsion formulation, the first silicone compound or the second silicone compound may react with moisture in the formulation in the presence of the catalyst in the second agent, and thus in terms of the stability of a formulation, it is preferable that both the first silicone compound and the second silicone compound are included in the first agent rather than in the second agent. The components in the first and second agents are not limited thereto, and the application thereof may be changed in consideration of technical aspects, provision of convenience and value to the user, or other necessary reasons.

In an embodiment, the two-component cosmetic composition for wrinkle improvement according to the present invention may be composed of: a first agent including the first silicone compound represented by Chemical Formula 1, the second silicone compound represented by Chemical Formula 3, and cerium oxide; and a second agent including the catalyst.

In this case, the catalyst may be comprised as a catalyst composition. In an embodiment, the first silicone compound and the second silicone compound may be included in the first agent in an amount of 1 to 40 parts by weight and 1 to 30 parts by weight, respectively, with respect to the total amount (100 parts by weight) of the first agent. In addition, the cerium oxide may be included in an amount of 0.1 to 8 parts by weight or 0.5 to 1.5 parts by weight in the first agent. Within the above content ranges, a coating having sufficient strength is formed to improve a scrubbing phenomenon caused by an external force, and a noticeable clouding phenomenon does not occur, and thus an excellent aesthetic effect and appropriate viscosity can be achieved.

In addition, the catalyst composition may be included in the second agent in an amount of 0.05 to 3 parts by weight or 0.1 to 2 parts by weight with respect to the total amount (100 parts by weight) of the second agent. In addition, the catalyst may be included in an amount of 0.001 to 0.06 parts by weight in the second agent and may be included in an amount of 10 to 600 ppm or 20 to 400 ppm in the second agent. Within the above content range, the catalyst can catalyze the reaction between the first silicone compound and the second silicone compound at room temperature.

In an embodiment, the first agent and the second agent may each be an anhydrous formulation in which moisture is not artificially added or an emulsion formulation, for example, W/O, O/W, W/O/W, O/W/O, W/S, S/W, W/S/W, or S/W/S. Specifically, the first agent and the second agent may each be an anhydrous formulation, W/O, O/W, S/W, or W/S, or more specifically, an anhydrous formulation, W/S, or S/W. The above formulation is preferred due to providing compatibility of the formulation and durability of a coating after application.

In an embodiment, the first agent and the second agent may each further include one or more cosmetically acceptable carriers that are blended into general skin cosmetics. For example, oil, water, a surfactant, a humectant, lower alcohol, a thickener, a chelating agent, a colorant, a pigment, an opacifier, a wax, an organic/inorganic sunscreen, a preservative, a fragrance, and the like may be appropriately blended thereof.

In the two-component cosmetic composition for wrinkle improvement according to the present invention, the first agent and the second agent are not limited to specific cosmetic forms and may be prepared in various forms such as base cosmetics and color cosmetics including liquid foundations, cushion foundations, concealers, mask packs, and the like by a method conventionally used in the art.

In an embodiment, the first agent and the second agent may each have a viscosity or kinematic viscosity of 10,000 to 2,000,000 cps or cSt, specifically, 20,000 to 1,000,000 cps or cSt or 30,000 to 500,000 cps or cSt. As a first silicone compound, a second silicone compound, and/or a filler is blended into the formulation (the first agent or the second agent) to enhance the strength of a coating, the viscosity of the resulting formulation tends to increase. Therefore, as the viscosity of the formulation is higher, a sturdier coating is formed, but when the viscosity of the formulation exceeds 2,000,000 cps or cSt, applicability is degraded, which makes uniform application in order to impart smooth skin difficult. In addition, when the viscosity of the formulation is less than 10,000 cps or cSt, the thermal stability of the formulation is degraded, and in the case of an emulsion formulation, phase separation of the formulation is likely to occur, which affects storage, handling, transportation, and use with respect to an end user.

In addition, the present invention relates to a method of using the above-described two-component cosmetic composition for wrinkle improvement.

In an embodiment, it is intuitive and preferable that the amount of the first agent and second agent used, that is, a mixing ratio according to the amount of the first agent and second agent used, is an integer ratio, especially, a ratio of 1:1 to obtain convenience with respect to a consumer. However, the amount of the first agent and second agent used and the resulting mixing ratio are not limited to 1:1 and may be adjusted in consideration of technical aspects, provision of convenience and value to a user, or other necessary reasons.

In an embodiment, a method for application on the skin, that is, an application order, is not particularly limited, and the application order of the first agent and the second agent may be changed in consideration of technical aspects, provision of convenience and value to the user, or other necessary reasons and may be selected, for example, from a method in which the second agent is applied after the first agent is applied, a method in which the first agent is applied after the second agent is applied, or a method in which the first agent and the second agent are first mixed and the mixture is applied on the skin. However, in view of the fact that curing is initiated when the first agent and the second agent come into contact with each other, it is more advantageous to apply the first agent first to form an even surface and then apply the second agent afterwards to produce a smooth skin surface.

Hereinafter, the present invention will be described in detail through examples. However, the following examples are merely presented to exemplify the present invention, and the scope of the present invention is not limited to the following examples. That is, the examples of the present invention serve to complete the disclosure of the present invention and are provided to fully inform the scope of the invention to those of ordinary knowledge and skill in the art to which the present invention pertains. The present invention should be defined based on the scope of the appended claims.

EXAMPLES

Raw materials, preparation methods, and formulations used in the examples and comparative examples of the present invention are presented to help in terms of understanding of the present invention, and raw materials, preparation methods, and formulations, which are used for an RTV-2 formulation of the present invention using cerium oxide as an inorganic filler, are not limited thereto.

Examples 1 to 6 and Comparative Examples 1 to 6. Preparation of the First Agent and the Second Agent First agents were prepared according to components and contents described in Tables 1 and 2, and the second agent was prepared according to components and contents described in Table 3. In all of the examples and comparative examples, the same second agent was used.

Components 16 and 17, that is, Valida Visco S+ and FM05-V, shown in Tables 1 and 2 are cellulose fibers, wherein the Valida Visco S+ has an average fiber length of about 5 μm and an average width of 10 to 15 nm, and the FM05-V has a maximum length of 100 μm and an average width of 10 to 100 nm.

In addition, as Component 10, that is, a Pt catalyst composition, shown in Table 3, a platinum(tetramethyldivinyldisiloxane) solution in 200 cSt vinyl-terminated poly(dimethylsiloxane) (2% Pt) commercially available from Johnson Matthey was used. The INCI names of commercially available components used in preparation of the first agent and second agent according to the examples and comparative examples are summarized in the following Table 4.

TABLE 1

| No. (wt %) | Example 1 | Example 2 | Example 3 | Example 4 | Example 5 | Example 6 |
|---|---|---|---|---|---|---|
| 1 Andisil VS 500 | 6.04 | 6.04 | 6.04 | 6.04 | 6.04 | 6.04 |
| 2 SF1202 | 5.52 | 5.52 | 5.52 | 5.52 | 5.52 | 5.52 |
| 3 Caprylyl methicone | 3.00 | 3.00 | 3.00 | 3.00 | 1.50 | 3.00 |
| 4 Ceratect NF | | | | | | 1.00 |
| 5 Ceratect NF-SA | 1.00 | 0.50 | 2.00 | 3.00 | 4.00 | |
| 6 SI01-4 ZnO-350 | | | | | | |
| 7 MT-700Z | | | | | | |
| 8 Aerosil R812S | | | | | | |
| 9 Andisil XL 10 | 6.42 | 6.42 | 6.42 | 6.42 | 6.42 | 6.42 |
| 10 Gransil EP-LS | 3.35 | 3.35 | 3.35 | 3.35 | 3.35 | 3.35 |
| 11 Andisil VS 65K | 17.90 | 17.90 | 17.90 | 17.90 | 17.90 | 17.90 |
| 12 KSG-210 | 6.04 | 6.04 | 6.04 | 6.04 | 6.04 | 6.04 |
| 13 Velvesil DM | 3.35 | 3.35 | 3.35 | 3.35 | 3.35 | 3.35 |
| 14 Seppiplus 400 | 1.12 | 1.12 | 1.12 | 1.12 | 1.12 | 1.12 |
| 15 water | 34.05 | 34.55 | 33.05 | 32.05 | 32.55 | 34.05 |
| 16 Valida Visco S+ | | | | | | |
| 17 FM05-V | | | | | | |
| 18 Gran Hydrogel O-HD | 6.21 | 6.21 | 6.21 | 6.21 | 6.21 | 6.21 |
| 19 ANYBES | 6.00 | 6.00 | 6.00 | 6.00 | 6.00 | 6.00 |
| Total | 100.00 | 100.00 | 100.00 | 100.00 | 100.00 | 100.00 |

TABLE 2

| No. (wt %) | Comparative Example 1 | Comparative Example 2 | Comparative Example 3 | Comparative Example 4 | Comparative Example 5 | Comparative Example 6 |
|---|---|---|---|---|---|---|
| 1 Andisil VS 500 | 6.04 | 6.04 | 6.04 | 6.04 | 6.04 | 6.04 |
| 2 SF1202 | 6.52 | 5.52 | 5.52 | 5.52 | 3.52 | 3.52 |
| 3 Caprylyl methicone | 3.00 | 3.00 | 3.00 | 3.00 | 3.00 | 3.00 |
| 4 Ceratect NF | | | | | | |
| 5 Ceratect NF-SA | | | | | | |

TABLE 2-continued

| No. (wt %) | Comparative Example 1 | Comparative Example 2 | Comparative Example 3 | Comparative Example 4 | Comparative Example 5 | Comparative Example 6 |
|---|---|---|---|---|---|---|
| 6 SI01-4 ZnO-350 | | 1.00 | | | | |
| 7 MT-700Z | | | 1.00 | | | |
| 8 Aerosil R812S | | | | 1.00 | | |
| 9 Andisil XL 10 | 6.42 | 6.42 | 6.42 | 6.42 | 6.42 | 6.42 |
| 10 Gransil EP-LS | 3.35 | 3.35 | 3.35 | 3.35 | 3.35 | 3.35 |
| 11 Andisil VS 65K | 17.90 | 17.90 | 17.90 | 17.90 | 17.90 | 17.90 |
| 12 KSG-210 | 6.04 | 6.04 | 6.04 | 6.04 | 6.04 | 6.04 |
| 13 Velvesil DM | 3.35 | 3.35 | 3.35 | 3.35 | 3.35 | 3.35 |
| 14 Seppiplus 400 | 1.12 | 1.12 | 1.12 | 1.12 | 1.12 | 1.12 |
| 15 water | 34.05 | 34.05 | 34.05 | 34.05 | 24.57 | 27.05 |
| 16 Valida Visco S+ | | | | | 12.48 | |
| 17 FM05-V | | | | | | 10.00 |
| 18 Gran Hydrogel 0-HD | 6.21 | 6.21 | 6.21 | 6.21 | 6.21 | 6.21 |
| 19 ANYBES | 6.00 | 6.00 | 6.00 | 6.00 | 6.00 | 6.00 |
| Total | 100.00 | 100.00 | 100.00 | 100.00 | 100.00 | 100.00 |

TABLE 3

| No. | (wt %) | |
|---|---|---|
| 1 | water | 25.00 |
| 2 | MILCOSIDE 301 | 0.49 |
| 3 | 1,3-Butylene glycol | 29.58 |
| 4 | Glycerin | 3.94 |
| 5 | NaCl | 0.99 |
| 6 | ANYBES | 4.64 |
| 7 | KSG-210 | 9.86 |
| 8 | KSG-016F | 9.86 |
| 9 | SF1202 | 14.64 |
| 10 | Pt catalyst | 1.00 |
| | Total | 100.00 |

TABLE 4

| Product name | INCI name |
|---|---|
| Andisil VS 500 | Vinyl dimethicone |
| SF1202 | Cyclopentasiloxane |
| Ceratect NF-SA | Cerium oxide, Stearic acid |
| Ceratect NF | Cerium oxide |
| SI01-4 ZnO-350 | Zinc oxide, Hydrogen dimethicone |
| MT-700Z | Titanium dioxide, Aluminum hydroxide, Stearic acid |
| Aerosil R812S | Silica silylate |
| Andisil XL 10 | Hydrogen dimethicone |
| Gransil EP-LS | Polysilicone-11, Laureth-12 |
| Andisil VS 65K | Vinyl dimethicone |
| KSG-210 | Dimethicone, Dimethicone/PEG-10/15 crosspolymer |
| Velvesil DM | Dimethicone, Cetearyl dimethicone crosspolymer |
| Seppiplus 400 | Polyacrylate 13/Polyisobutene/Polysorbate |
| Valida Visco S+ | Cellulose |
| FM05-V | Cellulose |
| Gran Hydrogel O-HD | Water, Glyceryl polyacrylate, 1,2-Hexandiol |
| ANYBES | Nylon-12 |
| MILCOSIDE 301 | Coco glucoside |
| KSG-016F | Dimethicone, Dimethicone/Vinyl Dimethicone crosspolymer |

The first agent and the second agent were prepared as follows.

[Preparation of first agent]

1) Components 1 to 8 were weighed in a container and mixed using a spatula.

2) Components 9 and 10 were added to the result of 1) and mixed using a spatula.

3) Components 11 to 14 were added to the result of 2), mixed using a spatula, and then stirred at 1000 rpm for 2 minutes using Homogenizing Disper commercially available from Primix Corporation. (oil phase A)

4) Components 15 to 17 were weighed in a separate container and then stirred at 2500 rpm for 5 minutes using Homogenizing Disper commercially available from Primix Corporation.

5) Component 18 was added to the result of 4) and then stirred at 2500 rpm for 2 minutes.

6) Component 19 was added while stirring the result of 5) at 2500 rpm and then stirred at 2500 rpm for 2 minutes. (aqueous phase B)

7) The aqueous phase B was slowly added while stirring the oil phase A at 700 rpm using Homogenizing Disper commercially available from Primix Corporation, and then stirred at 700 rpm for 2 minutes.

8) The result of 7) was stirred at 2500 rpm for 5 minutes.

[Preparation of Second Agent]

1) Components 1 to 5 were weighed in a container and stirred at 750 rpm for 2 minutes using Homogenizing Disper commercially available from Primix Corporation.

2) Component 6 was added while stirring the result of 1) at 750 rpm and then stirred at 750 rpm for 2 minutes. (aqueous phase C)

3) Components 7 to 9 were weighed in a separate container and then stirred at 750 rpm for 2 minutes using Homogenizing Disper commercially available from Primix Corporation. (oil phase D)

4) The aqueous phase C was slowly added while stirring the oil phase D at 750 rpm, and then stirred at 1000 rpm for 3 minutes.

5) The result of 4) was stirred at 2500 rpm for 5 minutes. (emulsion E)

6) Component 10 was added to the emulsion E and then stirred at 2500 rpm for 4 minutes.

Experimental Example 1. Tensile Experiment (1) Method

Each first agent prepared in the Examples and Comparative Examples was applied on a substrate, and then the second agent was applied on the applied first agent and cured to prepare a coating. The coating had an average thickness of 70 to 120 μm. When the thickness of the coating is below the above range, the coating is severely damaged when detached from the substrate, and thus it may be difficult to use the coating in a tensile experiment, and when the thickness is above the said range, it may be somewhat high to simulate a coating for application on the skin.

The prepared coating was processed into a dumbbell-shaped sample having an overall length of 115 mm, an overall width of 19 mm, and a distance between grips of 65 mm. The shape of the processed sample and the dimensions of each part comply with the Type IV standard of ASTM D638.

Each of the prepared dumbbell-shaped samples for the tensile experiment (Examples and Comparative Examples) was separated from the substrate, the thickness thereof was measured, and the force was measured with a load cell according to an elongation length, recorded using the TA-XT plus commercially available from Stable Micro Systems and summarized as Excel data. The elongation speed of the sample was set to 4 mm/s. Based on the stored Excel data and the length, width, and thickness of the sample, a stress value according to strain was calculated when force, measured with a load cell according to an elongation length, was applied. In this experiment, the strain is a value obtained by dividing the measured elongation distance L1 by the initial distance between grips of the sample L0, and the stress is a value obtained by dividing the force measured with a load cell by the cross-sectional area of the sample. In each of the Examples and Comparative Examples, the number of samples used for the tensile experiment was 5 or more.

(2) Results

Through the above-described tensile experiment and the processing of the data, the breaking stress (i.e., force that was applied on the cross section just before the coating was broken) and breaking strain (i.e., maximum elongation length measured just before the coating was broken) of the coating when the first agent and the second agent were polymerized were obtained.

The results of measuring the breaking stress are shown in FIGS. 2 and 3, and the results of measuring the breaking strain are shown in FIGS. 4 and 5. The units of the breaking stress of FIGS. 2 and 3 are kPa, and the breaking strain of FIGS. 4 and 5 represents the increase in distance (in percentage) between the grips of the sample relative to the initial distance. That is, when the breaking strain of FIG. 5 is, for example, 100% and the initial distance between the grips of the sample is 65 mm, the sample is ruptured after being elongated by 65 mm compared to the state before the measurement. In FIGS. 2, 3, 4, and 5, the values of error bars indicate the maximum and minimum values of the measured values.

As shown in FIG. 2, when $CeO_2$ was used as an inorganic filler, a breaking stress value was about 1.81 times higher than that when an inorganic filler was not added (Comparative Example 1), that is, a coating with the same area was able to withstand about 1.8 times more force before being broken. In addition, it can be confirmed that the improvement in the mechanical property due to $CeO_2$ was very significant compared to other fillers.

In addition, as shown in FIG. 3, it can be confirmed that Example 1 using surface-treated $CeO_2$ at 1% and Example 6 using surface-untreated $CeO_2$ at 1% exhibited excellent properties compared to Comparative Example 1 using no filler, and particularly, the properties were superior when the surface was treated.

That is, when the surface of hydrophilic surface-untreated $CeO_2$ is modified, $CeO_2$ particles are suppressed in terms of being re-agglomerated, $CeO_2$ dispersibility in the formulation can be improved, and filler-polymer interaction can be improved. Therefore, surface treatment can improve the mechanical properties of the coating.

In addition, as shown in FIG. 4, it can be confirmed that the breaking strain of the coating, that is, the maximum length of the coating in terms of being elongated before being broken, was most excellent when $CeO_2$ was used as a filler, and it can be seen that there is room for an increase of about 1.37 times as compared to the breaking strain value in the case of not adding a filler (Comparative Example 1).

In addition, as shown in FIG. 5, it can be confirmed that when the surface of $CeO_2$ was modified, the mechanical properties of the coating could be improved.

That is, it can be seen that the coating property improvement effect resulting from the addition of cerium oxide as a filler is excellent.

Experimental Example 2. Colorimeter Measurement (1) Method

In order to measure the degree of clouding resulting from the formation of the coating, the first agent was applied with a thickness of 150 μm on a Form 2A opacity chart commercially available from Leneta Co Inc., the second agent was applied with a thickness of 150 μm thereon, and curing was performed.

For the coating formed on the opacity chart, the L, a, and b values according to the CIELAB color space, that is, the brightness, red-green, and yellow-blue data, of the black surface and white surface of the opacity chart were measured using a CM-512m3 colorimeter commercially available from Minolta. Each measured value was an average value of three consecutive measurements. In the measurement of the measured values, the angle that the light source, the measurement sample surface, and the detector formed was 45 degrees.

ΔE was calculated using the L, a, and b values measured for the black surface and white surface, and the calculation equation is represented as Equation 1. In Equation 1, $L_{black}$ and $L_{white}$ represent measured L values of the black surface and the white surface, respectively, $a_{black}$ and $a_{white}$ represent measured a values of the black surface and the white surface, respectively, $b_{black}$ and $b_{white}$ represent measured b values of the black surface and the white surface, respectively, and SQRT refers to the square root of the value in parentheses that is modified by SQRT.

$$\Delta E = \mathrm{SQRT}((L_{black}-L_{white})^2+(a_{black}-a_{white})^2+(b_{black}-b_{white})^2) \quad \text{[Equation 1]}$$

(2) Results

The above-described colorimeter measurement results are shown in Tables 5 and 6. The measurement result of an opacity chart on which the coating was not applied (blank) was denoted as $\Delta E_{blank}$.

TABLE 5

| | blank | Example 1 | Example 2 | Example 3 | Example 4 | Example 5 |
|---|---|---|---|---|---|---|
| $\Delta E$ | 86.40 | 68.63 | 70.75 | 55.96 | 53.75 | 50.45 |
| $\Delta E_{blank}$ − $\Delta E$ | 0.00 | 17.78 | 15.65 | 30.44 | 32.65 | 35.95 |

TABLE 6

| | blank | Comparative Example 1 | Comparative Example 2 | Comparative Example 3 | Comparative Example 4 | Comparative Example 5 | Comparative Example 6 |
|---|---|---|---|---|---|---|---|
| $\Delta E$ | 86.40 | 76.47 | 72.96 | 56.26 | 75.95 | 75.91 | 75.48 |
| $\Delta E_{blank}$ − $\Delta E$ | 0.00 | 9.94 | 13.44 | 30.14 | 10.45 | 10.49 | 10.93 |

As shown in Tables 5 and 6, a value obtained by subtracting $\Delta E$ of each coating from $\Delta E_{blank}$, that is, $\Delta E_{blank}-\Delta E$, was the highest at 30.14 in the case of utilizing $TiO_2$ (Comparative Example 3) and was small at 9.94 when a filler was not added (Comparative Example 1). In the case of Example 1 using $CeO_2$, the value was 17.78.

Particularly, Example 2 using 0.5% $CeO_2$ exhibited higher breaking stress and breaking strain compared to Comparative Example 2 using 1% ZnO, whereas the $\Delta E_{blank}-\Delta E$ values were similar at 13.44 and 15.65 respectively.

Therefore, it can be seen that when $CeO_2$ is used, it is possible to prepare a coating that exhibits less cloudiness compared to when the same amount of $TiO_2$ is added, and thus the amount of $CeO_2$ added can be more easily increased compared to $TiO_2$ in terms of reducing a clouding phenomenon.

That is, when cerium oxide is used as an inorganic filler, even use of a smaller amount of inorganic filler can reinforce mechanical strength and minimize a clouding phenomenon.

Experimental Example 3. Viscosity Measurement (1) Method

In order to measure the change in viscosity of the formulation, the viscosity of the first agent was measured using LVT230 commercially available from Brookfield. In this case, the spindle number was 64, the speed dial of the viscometer was set to 3, and a scale value was recorded after waiting until an equilibrium state was reached without making any changes to the scale of the viscometer.

(2) Results

The results of measuring the viscosity of the formulation are shown in FIG. 6. In FIG. 6, the units are provided as cps units.

As shown in FIG. 6, it can be confirmed that when cellulose is used (Comparative Examples 5 and 6), even comprising only 1% of cellulose in the formulation increased the viscosity substantially compared to when no fillers or other fillers were added.

A problem such as an increase in the viscosity of the formulation not only requires additional effort in dispersing the filler during preparation, but also causes the viscosity of the prepared first agent or second agent to exceed an appropriate range, which makes it difficult to achieve uniform application of the formation to provide an ideal coating.

Through the experimental examples according to the present invention, it can be seen that when cerium oxide is added as an inorganic filler, the mechanical properties of the formulation can be significantly increased, a noticeable clouding phenomenon is not shown, and viscosity can be easily controlled.

INDUSTRIAL APPLICABILITY

The two-component cosmetic composition for wrinkle improvement according to the present invention forms a coating having strength sufficient to improve a scrubbing phenomenon caused by an external force, does not show a noticeable clouding phenomenon, and has appropriate viscosity.

The invention claimed is:

1. A two-component cosmetic composition for wrinkle improvement, comprising a first silicone compound, a second silicone compound, cerium oxide ($CeO_2$), and a catalyst and composed of a first agent and a second agent, wherein the second agent includes the catalyst and does not include the catalyst, the first silicone compound, and the second silicone compound at the same time, wherein the first agent comprises the first silicone compound, the second silicone compound, and the cerium oxide, wherein the first silicone compound comprises vinyl dimethicone, wherein the second silicone compound comprises hydrogen dimethicone, and wherein the cerium oxide is surface-modified with stearic acid.

2. The two-component cosmetic composition for wrinkle improvement according to claim 1, wherein the catalyst is a metal catalyst including a metal ion or a metal atom in a molecular or crystalline structure.

3. The two-component cosmetic composition for wrinkle improvement according to claim 1, wherein the cerium oxide has an average particle diameter of 50 nm to 20 μm.

4. The two-component cosmetic composition for wrinkle improvement according to claim 1, wherein the first silicone compound and the second silicone compound are each included in an amount of 1 to 40 parts by weight with respect to the weight of the first agent, the cerium oxide is included in an amount of 0.1 to 8 parts by weight with respect to the weight of the first agent, and the catalyst is included in an amount of 0.001 to 0.06 parts by weight with respect to the weight of the second agent.

5. The two-component cosmetic composition for wrinkle improvement according to claim 1, wherein the first agent and the second agent are each an anhydrous formulation or an emulsion formulation, and the emulsion formulation is W/O, O/W, W/O/W, O/W/O, W/S, S/W, W/S/W, or S/W/S.

6. The two-component cosmetic composition for wrinkle improvement according to claim 1, wherein the first agent and the second agent each have a viscosity of 10,000 to 2,000,000 cps and a kinematic viscosity of 10,000 to 2,000,000 cSt.

7. A method of improving wrinkles using the two-component cosmetic composition for wrinkle improvement according to claim 1, the method comprising:

applying a first agent on the skin; and applying a second agent on the applied first agent.

8. A two-component cosmetic composition for wrinkle improvement, comprising a first silicone compound, a second silicone compound, cerium oxide ($CeO_2$), and a catalyst and composed of a first agent and a second agent, wherein the second agent includes the catalyst and does not include the catalyst, the first silicone compound, and the second silicone compound at the same time, wherein the first silicone compound comprises vinyl dimethicone, wherein the second silicone compound comprises hydrogen dimethicone, and wherein the cerium oxide is surface-modified with stearic acid and is comprised in an amount of 1 to 4 parts by weight with respect to the weight of the first agent.

* * * * *